United States Patent [19]

Fünfschilling et al.

[11] Patent Number: 5,759,443
[45] Date of Patent: Jun. 2, 1998

[54] CYCLOPENTYL DERIVATIVES

[75] Inventors: Jürg Fünfschilling; Alois Villiger, both of Basel, Switzerland

[73] Assignee: Rolic AG, Zug, Switzerland

[21] Appl. No.: 883,189

[22] Filed: Jun. 26, 1997

[30] Foreign Application Priority Data

Jul. 26, 1996 [EP] European Pat. Off. .......... 96112064

[51] Int. Cl.$^6$ .................. C09K 19/34; C09K 19/30; C07D 239/02; C07D 211/70
[52] U.S. Cl. .................. 252/299.61; 252/299.62; 252/299.63; 252/299.66; 252/299.65; 252/299.67; 252/299.6; 544/298; 544/335; 546/339; 546/342; 549/369; 549/29; 548/136; 568/647; 568/626
[58] Field of Search .................. 252/299.63, 299.61, 252/299.6, 299.62, 299.65, 299.66, 299.67; 544/298, 335; 546/339, 342, 152, 154; 548/136; 560/60, 102; 568/647, 626; 549/29, 369, 370

[56] References Cited

U.S. PATENT DOCUMENTS

| | | | |
|---|---|---|---|
| 4,873,019 | 10/1989 | Krause et al. | 252/299.61 |
| 5,068,389 | 11/1991 | Wachtler et al. | 558/411 |
| 5,269,965 | 12/1993 | Matsumara et al. | 252/299.63 |
| 5,370,821 | 12/1994 | Matsumara et al. | 252/299.63 |

FOREIGN PATENT DOCUMENTS

| | | |
|---|---|---|
| 4 027 923 A1 | 3/1991 | European Pat. Off. . |
| 2 220 658 | 1/1990 | United Kingdom . |

OTHER PUBLICATIONS

English language Abstract of Hittichi et al., DE 4 027 923, 1991.

*Primary Examiner*—C. H. Kelly
*Attorney, Agent, or Firm*—Bryan Cave LLP

[57] ABSTRACT

Objects of this invention are cyclopentyl compounds of the general formula

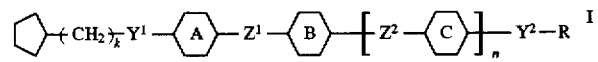

wherein k signifies a whole number of 4 to 18;

n signifies 0 or 1;

$Y^1$, $Y^2$ signify a single bond, —O—, —COO— or —OOC—;

rings A, B, C each independently signify optionally mono- or difluorinated 1,4-phenylene, pyrimidine-2,5-diyl, pyridine-2,5-diyl, pyrazine-2,5-diyl, naphthalene-2,6-diyl, quinoline-2,6-diyl, thiophene-2,5-diyl, thiazole-2,5-diyl or 1,3,4-thiadiazole-2,5-diyl and ring C also signifies trans-1,4-cyclohexylene or trans-1,3-dioxane-2,5-diyl;

$Z^1$ signifies a single bond, —COO—, —OOC— or —C≡C—;

$Z^2$ signifies —COO—, —OOC—, —OCH$_2$—, —CH$_2$O— or —(CH$_2$)$_2$—; and

R signifies straight-chain or branched, optionally optically active, alkyl or alkenyl with 4 to 20 carbon atoms in which one or two non-adjacent methylene groups can be replaced by —O—, —COO—, —OOC— and/or epoxyethylene and/or at least one hydrogen can be replaced by fluorine and/or one hydrogen can be replaced by chlorine or cyano and/or a terminal hydrogen can be replaced by cyclopentyl.

mixtures containing such compounds as well as electrooptical devices containing these compounds.

46 Claims, No Drawings

CYCLOPENTYL DERIVATIVES

FIELD OF THE INVENTION

The invention relates to cyclopentyl compounds, liquid crystalline mixtures which contain such compounds and the use of such compounds and mixtures for optical and electro-optical devices.

BACKGROUND

Liquid crystals are used primarily as dielectrics in electro-optical display devices, since the optical properties of such substances can be influenced by an applied voltage. Such electro-optical devices can be based on various physical effects. For example, cells having dynamic scattering, DAP cells (deformation of aligned phases), guest/host cells, TN cells ("twisted nematic"), STN cells ("super twisted nematic"), SBE cells ("super birefringents effect"), OMI cells ("optical mode interference") and actively addressed AM-LCD's ("active matrix liquid crystal displays", thin film transistor addressed cells) are known.

In addition to the aforementioned types of cell, the properties of which are based on the use of nematic or cholesteric liquid crystals, display devices which are based on the principle of ferroelectric tilted chiral-smectic phases are also known. Suitable tilted chiral-smectic phases are, for example, $S_C^*$, $S_F^*$ and $S_I^*$ phases, of which the $S^*_C$ phase facilitates the shortest response times because of its lower viscosity. Known types of cell which are based on the principle of $S_C^*$ phases are, for example, SSF cells ("surface stabilized ferroelectric"), SBF cells ("short-pitch bistable ferroelectric") or DHF cells ("deformed helix ferroelectric").

Liquid crystal mixtures must have a good chemical and thermal stability and a high stability towards electric and magnetic fields. Further, they should have suitable mesophases over a broad temperature range, a low viscosity and short response times. Materials based on tilted chiral-smectic phases should, moreover, have a sufficiently high spontaneous polarization and, depending on the type of cell, a twisting capacity which is rather small (for SSF cells) or as high as possible (for SBF and DHF cells). In order to facilitate the orientation in the cells, they can also preferably have a $S_A$ phase above the $S_C^*$ phase. In the case of DHF cells a large switching angle between the two stable states is of great advantage for the production of a disturbance-free image.

As ferroelectric liquid crystal mixtures there are primarily suitable mixtures of at least one optically active dopant and a liquid crystal material which comprises several achiral components which usually have a broad tilted-smectic phase, preferably a $S_C$ phase. The optically active dopants need not themselves be liquid crystalline, but they preferably have smectic or cholesteric phase(s). The concentration of the optically active dopants is chosen such that a chiral tilted-smectic phase (i.e. usually a $S_C^*$ phase) with suitable twisting as well as a sufficiently high spontaneous polarization is induced.

SUMMARY OF THE INVENTION

The invention relates to cyclopentyl compounds of the general formula

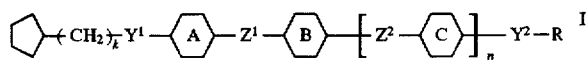

wherein k is a whole number of 4 to 18;

n is 0 or 1;

$Y^1, Y^2$ are, independently, a single bond, —O—, —COO— or —OOC—;

rings A, B, C each independently are 1,4-phenylene, pyrimidine-2,5-diyl, pyridine-2,5-diyl, pyrazine-2,5-diyl, naphthalene-2,6-diyl, quinoline-2,6-diyl, thiophene-2,5-diyl, thiazole-2,5-diyl or 1,3,4-thiadiazole-2,5-diyl, which are unsubstituted or mono- or difluorinated and ring C also signifies trans-1,4-cyclohexylene or trans-1,3-dioxane-2,5-diyl;

$Z^1$ is a single bond, —COO—, —OOC— or —C≡C—;

$Z^2$ is —COO—, —OOC—, —OCH$_2$—, —CH$_2$O— or —(CH$_2$)$_2$—; and

R is straight-chain or branched, optically inactive or optically active, alkyl or alkenyl with 4 to 20 carbon atoms in which one or two non-adjacent methylene groups can be replaced independently by —O—, —COO—, —OOC— or epoxyethylene, in which one or more hydrogen atoms can be replaced by fluorine, in which one hydrogen atom can be replaced by chlorine or cyano, and in which a terminal hydrogen atom can be replaced by cyclopentyl.

It has been found that the cyclopentyl compounds of formula I in accordance with the invention compared with conventional compounds which carry an ethyl or vinyl group in place of the terminal cyclopentane ring have not only slightly higher or comparable clearing points and upper limits of the $S_C$ phase, but surprisingly the switching angle is significantly increased without essentially influencing the switching times. Moreover, the compounds of formula I have a high chemical stability as well as a high stability towards electric and magnetic fields. They are colourless, can be produced in a simple manner and have a good mutual solubility and a good solubility in known liquid crystal materials. These properties ensure that the use of such compounds in ferroelectric DHF, SBF or SSF cells facilitates a disturbance-free image with a very high contrast and short response times.

DETAILED DESCRIPTION OF THE INVENTION

The term "straight-chain or branched, optically inactive or optically active, alkyl or alkenyl with 4 to 20 carbon atoms in which one or two non-adjacent methylene groups can be replaced independently by —O—, —COO—, —OOC— or epoxyethylene, in which one or more hydrogen atoms can be replaced by fluorine in which one or more hydrogen atoms can be replaced by chlorine or cyano, and in which a terminal hydrogen atom can be replaced by cyclopentyl" embraces in the scope of the invention residues such as alkyl, alkenyl, alkoxyalkyl, alkenyloxyalkyl, alkanoyloxyalkyl, alkoxycarbonyl-alkyl, fluoroalkyl, chloroalkyl, cyanoalkyl, trifluoromethyl-alkyl and ω-cyclopentyl-alkyl with 4 to 20 carbon atoms.

Compounds of formula I in which rings A, B and C each independently signify 1,4-phenylene, 2- or 3-fluoro-1,4-phenylene, 2,3-difluoro-1,4-phenylene, pyrimidine-2,5-diyl, pyridine-2,5-diyl or pyrazine-2,5-diyl and ring C also signifies trans-1,4-cyclohexylene or trans-1,3-dioxane-2,5-diyl are preferred. Compounds of formula I in which at least one of rings A, B and C signifies 1,4-phenylene, 2- or 3-fluoro-1,4-phenylene or 2,3-difluoro-1,4-phenylene and a maximum of one of rings A, B and C signifies pyrimidine-2,5-diyl, pyridine-2,5-diyl or pyrazine-2,5-diyl are especially preferred.

Compounds of the following formulae are particularly preferred

Further, compounds of formulas I and Ia–Ii in which k signifies a whole number of 5 to 12 are preferred. Preferably, $Y^1$ signifies a single bond, —O— or —COO—; compounds of formulas I and Ia–Ii in which $Y^1$ signifies —O— are especially preferred.

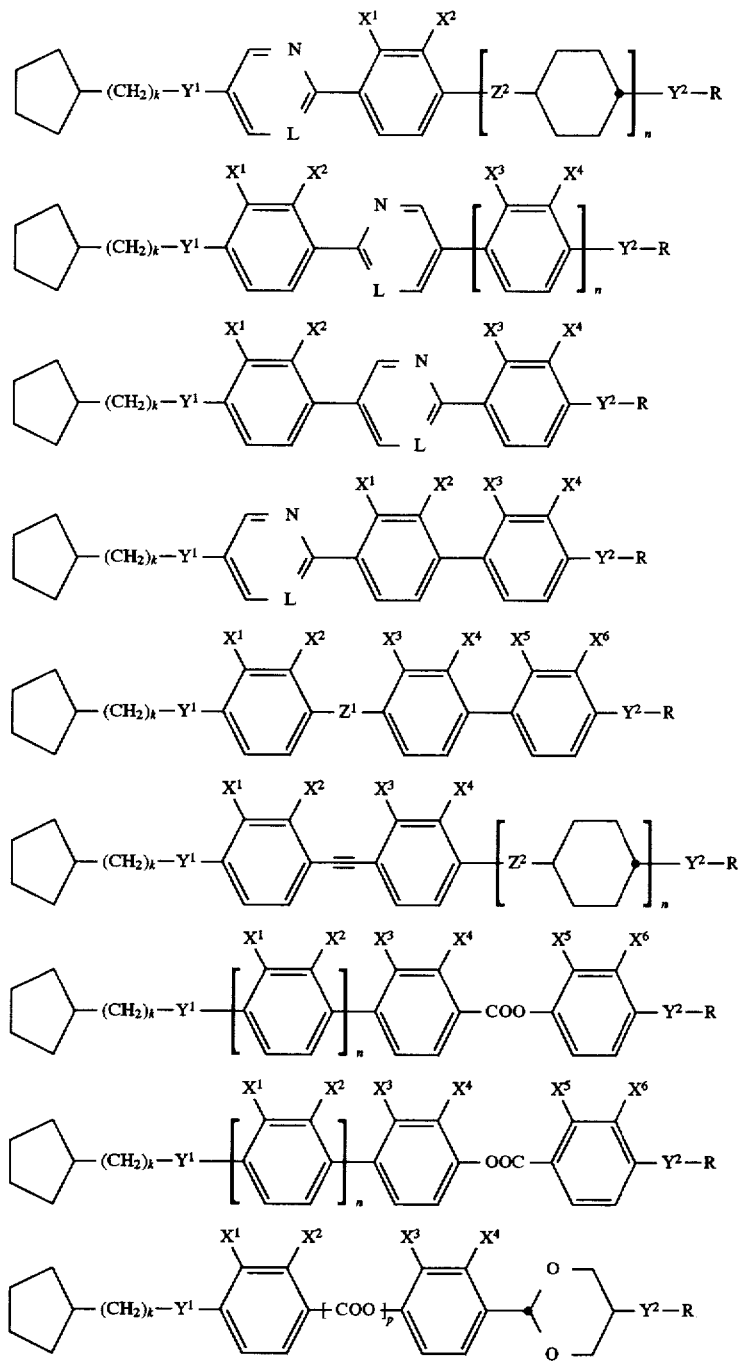

wherein

L is nitrogen or —CH═;

$X^1$–$X^6$ are, independently hydrogen or fluorine;

p is 0 or 1; and n, k, $Y^1$, $Y^2$ and R have the significances given above.

Depending on the significance of R, the compounds of formula I can be used as optically active dopants or as achiral mixture components for liquid crystal mixtures.

Especially suitable optically active compounds of formulas I and Ia–Ii are those compounds in which R signifies an alkyl or alkenyl residue with 5 to 12 carbon atoms in which 1 or 2 non-terminal methylene groups is/are replaced by —C*H(W)—, —C*F(CH$_3$)— and/or epoxyethylene and 1 or 2 non-adjacent methylene groups can be replaced by —O—, —COO—, —OOC—. W signifies fluorine, chlorine cyano, methyl or trifluoromethyl and C* signifies a chiral centre.

In especially preferred optically active compounds of formulas I and Ia–Ii the group —Y$^2$—R signifies an optically active group such as 2- or 3-fluoroalkyl, 2- or 3-fluoroalkoxy, 2,3-difluoroalkoxy, 2- or 3-fluoro-alkanoyloxy, 2,3-difluoro-alkanoyloxy, 2-fluoro-2-methyl-alkanoyloxy, 2-fluoro-3-methyl-alkanoyloxy, 2- or 3-chloro-alkoxy, 2- or 3-chloro-alkanoyloxy, 2-chloro-3-methylalkanoyloxy, 1- or 2-cyanoalkyl, 1- or 2-cyanoalkoxy, 2- or 3-cyano-alkanoyloxy, 1-, 2- or 3-methylalkyl, 1-, 2- or 3-methylalkoxy, 2- or 3-methyl-alkanoyloxy, 1-, 2- or 3-trifluoromethyl-alkanoyloxy, 1,2-epoxyalkyl, 2,3-epoxyalkoxy, 2,3-epoxy-alkanoyloxy, 1-alkoxycarbonyl-ethyl, 1-alkoxycarbonylethoxy, 2-alkoxy-propanoyloxy, (1-methyl-alkoxy)-carbonyl, (1-trifluoromethyl-alkoxy)-carbonyl, 1-alkoxy-2,2,2-trifluoroethyl or ω-trifluoromethyl-ω-alkoxyalkyl with in each case 5 to 12 carbon atoms.

As achiral mixture components for liquid crystal mixtures there are especially suitable compounds of general formulae I and Ia–Ii in which Y$^2$ signifies a single bond, —O— or —OOC— and R signifies a straight-chain or branched (racemic) alkyl or alkenyl residue with 5 to 12 carbon atoms in which a methylene group not adjacent to Y$^2$ can be replaced by —O—, —COO— or —OOC— and/or one or more hydrogen atoms can be replaced by fluorine and/or a terminal hydrogen atom can be replaced by cyclopentyl, such preferred residues are, for example, 4-, 5-, 6-, 7- or 8-methyl-alkyl, 1-, 2-, 3-, 4-, 5-, 6- or 7-alkenyl, ω-alkoxy-alkyl, ω-alkoxycarbonyl-alkyl, ω-alkanoyloxy-alkyl, ω-perfluoroalkyl-alkyl, ω-cyclopentyl-alkyl and the like.

Especially preferred optically inactive residues R are straight-chain or methyl-branched alkyl or alkenyl residues with 5 to 12 carbon atoms such as, for example, pentyl, hexyl, heptyl, octyl, nonyl, decyl, undecyl, dodecyl, 1-, 2-, 3- or 4-pentenyl, 1-, 2-, 3- or 4-hexenyl, 1-, 2-, 3-, 4- or 5-heptenyl, 1-, 2-, 3-, 4-, 5- or 6-octenyl, 1-, 2-, 3-, 4-, 5-, 6- or 7-nonenyl, 1-, 2-, 3-, 4-, 5-, 6- or 7-decenyl, 1-, 2-, 3-, 4-, 5-, 6- or 7-undecenyl, 1-, 2-, 3-, 4-, 5-, 6- or 7-dodecenyl, 4-methyl-hexyl, 4- or 5-methyl-heptyl, 4-, 5- or 6-methyl-octyl, 4-, 5-, 6- or 7-methyl-nonyl, 4-, 5-, 6-, 7- or 8-methyl-decyl, 4-, 5-, 6-, 7-, 8- or 9-methyl-undecyl, 4-, 5-, 6-, 7-, 8-, 9- or 10-methyl-dodecyl and the like.

The compounds of formula I in accordance with the invention can be produced in a manner known per se analogously to compounds which carry a hydrogen atom in place of the terminal cyclopentane ring. The manner in which the reaction is carried out depends largely on the functional groups in Y$^1$, Y$^2$, Z$^1$, Z$^2$ and R.

Compounds of formula I in which Y$^1$ signifies a single bond are preferably produced via a Wittig reaction of an intermediate of the formula

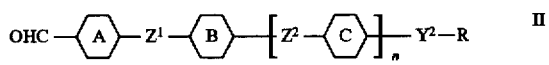

II with an (ω-cyclopentyl)-alkyl-triphenyl-phosphonium halide with the addition of an equivalent of a suitable base such as, for example, potassium tert.-butylate in an inert solvent such as, for example, tert.butyl methyl ether, diethyl ether or tetrahydrofuran, preferably between −20° C. and room temperature, and subsequent catalytic hydrogenation, for example, with palladium-on-charcoal in toluene and the like.

Compounds of formula I in which Y$^1$ signifies —O— can be produced by alkylating an intermediate of the formula

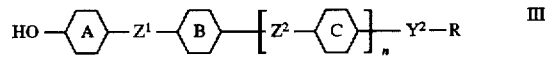

III with an (ω-bromo-alkyl)-cyclopentane and a suitable base such as, for example, potassium carbonate in a polar solvent such as, for example, DMF, ethyl methyl ketone or DMSO at a temperature between room temperature and 100° C., preferably at about 50° C.

Compounds of formula I in which Y$^1$ signifies —COO— can be produced by acylating an intermediate of formula III with an ω-cyclopentyl-alkanoic acid, for example in the presence of a slight excess of N,N'-dicyclohexyl-carbodiimide and a catalytic amount of 4-dimethylamino-pyridine in dichloromethane at 0° C. or room temperature.

The aforementioned processes are standard reactions in organic chemistry and will be known by a person skilled in the art. The intermediates which are used are known compounds or analogues of known compounds.

The compounds of formula I can be used in the form of mixtures with one another and/or with other liquid crystal components. The invention is accordingly also concerned with liquid crystalline mixtures having at least two components, with at least one component being a compound of formula I. A second component and further components which may be present can be other compounds of formula I or other suitable liquid crystal components. The compounds of formula I are preferably used as components of mixtures which have a tilted smectic phase, for example a S$_C$* phase. The compounds of formula I can thereby be used as optically inactive basic components and/or as optically active dopants.

Having regard to the good solubility of the compounds of formula I in accordance with the invention in other liquid crystal components and having regard to their good miscibility with one another, the content of compounds of formula I in the mixtures in accordance with the invention can be relatively high and can be, for example, 0.5–30 wt. %. When optically inactive compounds of formula I are used, then a content of about 2–30 wt. %, especially 3–25 wt. %, is generally preferred. The content of optically active dopants is determined largely by the twisting capacity, the spontaneous polarization and the desired pitch of the mixture. The content of optically active dopants of formula I which may be used can therefore vary in a wide range and can be, for example, 0.5–20 wt. %, especially about 1–15 wt. %.

Preferably, the mixtures in accordance with the invention contain, in addition to one or more compounds of formula I, one or more compounds from the group of compounds of the formulas

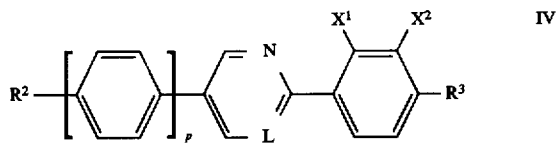

IV

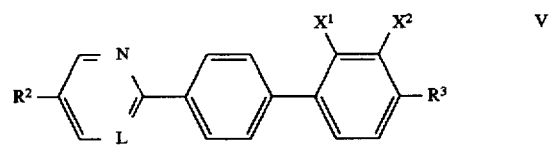

V

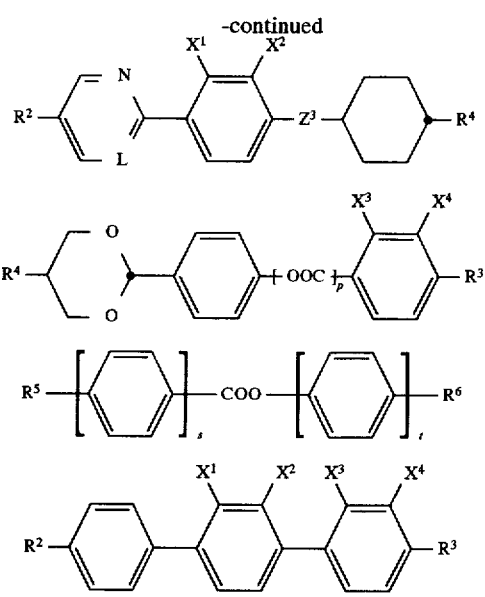

$Z^3$ signifies a single bond, —OOC—, —OCH$_2$— or —(CH$_2$)$_2$—;

$R^2$, $R^3$ each independently signify alkyl, alkenyl, alkoxy, alkoxyalkyl, alkenoyloxy, alkanoyloxy, alkenoyloxy, alkoxyalkoxy, alkoxycarbonyl or alkenyloxycarbonyl;

$R^4$ signifies alkyl or alkenyl; and $R^5$, $R^6$ each independently signify alkyl, alkenyl, alkoxy or alkenyloxy.

The substituents $R^2$ to $R^6$ can be straight-chain or branched, but they are preferably straight-chain. They have a maximum of 18 carbon atoms, preferably 5 to 12 carbon atoms.

The mixtures in accordance with the invention can additionally contain one or more optically active compounds from the group of compounds of the formulas

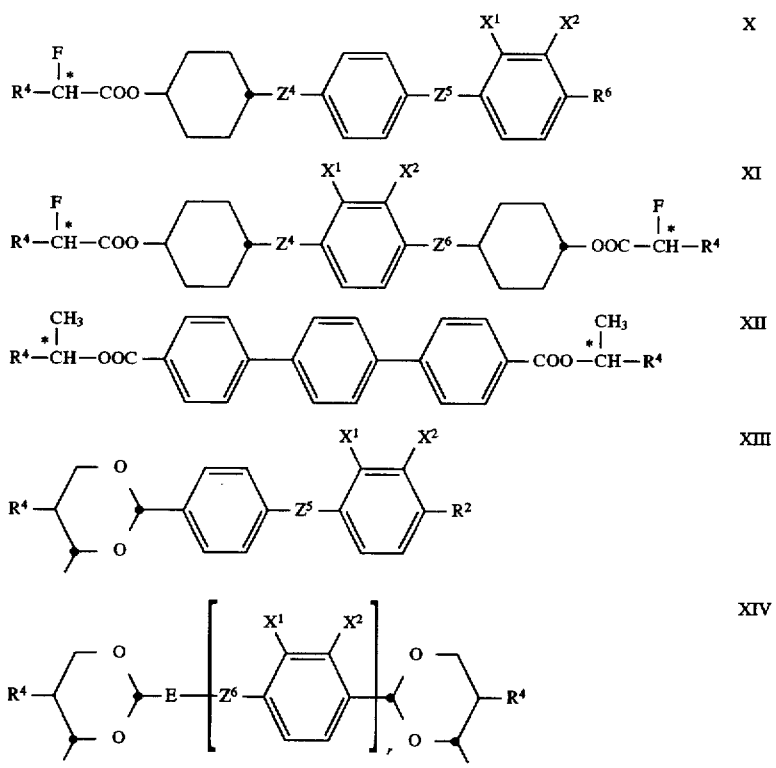

wherein p signifies 0 or 1;

s,t are 1 or 2, provided that s+t=2 or 3;

L signifies nitrogen or —CH=;

$X^1$, $X^2$, $X^3$, $X^4$ each independently signify hydrogen or fluorine;

wherein

E signifies 1,4-phenylene or trans-1,4-cyclohexylene;

r signifies 0, 1 or 2;

$Z^4$ signifies a single bond, —(CH$_2$)$_2$— or —CH$_2$O—;

$Z^5$ signifies a single bond, —OCH$_2$—, —COO— or —OOC—;

$Z^6$ signifies a single bond, —$(CH_2)_2$— or —$OCH_2$—; and the remaining symbols have the significances set forth above.

The production of the liquid crystalline mixtures and of the electro-optical devices can be effected in a known manner.

The production of the compounds of formula I and of liquid crystalline mixtures containing such compounds are illustrated in more detail by the following Examples. The abbreviations used for the characterization of the phase transitions have the following significances: C stands for crystalline, S, $S_A$, $S_C$ etc. stand for smectic, smectic A, smectic C etc., N stands for nematic and I stands for isotropic.

EXAMPLE 1

A mixture of 0.157 g of 4-(5-heptyl-2-pyridyl)-phenol, 0.153 g of (8-bromooctyl)-cyclopentane, 6 ml of dimethylformamide and 0.24 g of finely powdered potassium carbonate was stirred at 55° C. for 3 hours. The reaction mixture was partitioned between water and diethyl ether. The organic phase was washed with water and with saturated sodium chloride solution, dried over magnesium sulphate, filtered and the filtrate was concentrated. Chromatography of the crude product (0.28 g) on 10 g of silica gel with hexane/ethyl acetate 37:3 (v/v) and two-fold recrystallization of the product-containing fractions from 3 ml of hexane each time gave 0.16 g of pure 5-heptyl-2-[4-(8-cyclopentyl-octyloxy)-phenyl]-pyridine; m.p. (C-$S_I$) 38.3° C., $S_I$-$S_C$ 56.9° C., cl.p. ($S_C$-I) 72.6° C.

The (8-bromooctyl)-cyclopentane used as the starting material was prepared as follows:

2.4 g of N-bromosuccinimide were added portionwise to a solution of 2.27 g of cyclopentane-octanol and 3.22 g of triphenylphosphine in 40 ml of dichloromethane in an ice bath. The reaction mixture was left to stand at room temperature overnight, filtered and the filtrate was concentrated. The residue was partitioned between 50 ml of methanol/water (vol.) 4:1 and 40 ml of hexane and the methanol phase was separated. The hexane phase was washed twice with 20 ml of methanol/water 4:1 each time and concentrated. Distillation of the residue in a bulb-tube at 130°–150° C./0.05 Torr gave 2.3 g of (8-bromooctyl)-cyclopentane as a colorless oil.

The following compounds can be prepared analogously:
5-Octyl-2-[4-(8-cyclopentyl-octyloxy)-phenyl]-pyridine;
5-nonyl-2-[4-(8-cyclopentyl-octyloxy)-phenyl]-pyridine, m.p. (C-$S_I$) 53.2° C., $S_I$-$S_C$ 67.1° C., cl.p. ($S_C$-I) 77.0° C.;
5-decyl-2-[4-(8-cyclopentyl-octyloxy)-phenyl]-pyridine;
5-heptyl-2-[4-(7-cyclopentyl-heptyloxy)-phenyl]-pyridine, (C-$S_C$) 73.2° C., $S_I$-$S_C$ 70.0° C., cl.p. ($S_C$-I) 78.2° C.;
5-octyl-2-[4-(7-cyclopentyl-heptyloxy)-phenyl]-pyridine;
5-nonyl-2-[4-(7-cyclopentyl-heptyloxy)-phenyl]-pyridine, m.p. (C-$S_I$) 73.2° C., $S_I$-$S_C$ 78.9° C., cl.p. ($S_C$-I) 82.6° C.;
5-decyl-2-[4-(7-cyclopentyl-heptyloxy)-phenyl]-pyridine;
5-heptyl-2-[4-(6-cyclopentyl-hexyloxy)-phenyl]-pyridine;
5-nonyl-2-[4-(6-cyclopentyl-hexyloxy)-phenyl]-pyridine;
5-nonyl-2-[4-(5-cyclopentyl-pentyloxy)-phenyl]-pyridine;
5-heptyl-2-[4-(9-cyclopentyl-nonyloxy)-phenyl]-pyrimidine;
5-heptyl-2-[4-(8-cyclopentyl-octyloxy)-phenyl]-pyrimidine;
5-octyl-2-[4-(8-cyclopentyl-octyloxy)-phenyl]-pyrimidine, m.p. (C-$S_C$) 40.2° C., $S_C$-$S_A$ 55.6° C., $S_A$-N 57.6° C., cl.p. (N-I) 61.5° C.;
5-nonyl-2-[4-(8-cyclopentyl-octyloxy)-phenyl]-pyrimidine, m.p. (C-$S_C$) 50.6° C., $S_C$-$S_A$ 63.6° C., cl.p. ($S_A$-I) 61.5° C.;
5-decyl-2-[4-(8-cyclopentyl-octyloxy)-phenyl]-pyrimidine;
5-heptyl-2-[4-(7-cyclopentyl-heptyloxy)-phenyl]-pyrimidine;
5-octyl-2-[4-(7-cyclopentyl-heptyloxy)-phenyl]-pyrimidine, m.p. (C-$S_C$) 52.7° C., $S_C$-N 57.5° C., cl.p. (N-I) 66.0° C.;
5-nonyl-2-[4-(7-cyclopentyl-heptyloxy)-phenyl]-pyrimidine, m.p. (C-$S_C$) 57.5° C., $S_C$-$S_A$ 68.6° C., $S_A$-N 70.4° C., cl.p. (N-I) 71.1° C.;
5-decyl-2-[4-(7-cyclopentyl-heptyloxy)-phenyl]-pyrimidine;
5-octyl-2-[4-(6-cyclopentyl-hexyloxy)-phenyl]-pyrimidine;
5-nonyl-2-[4-(6-cyclopentyl-hexyloxy)-phenyl]-pyrimidine;
5-nonyl-2-[4-(5-cyclopentyl-pentyloxy)-phenyl]-pyrimidine;
5-heptyl-2-[4-(7-cyclopentyl-heptyloxy)-3-fluoro-phenyl]-pyrimidine;
5-octyl-2-[4-(7-cyclopentyl-heptyloxy)-3-fluoro-phenyl]-pyrimidine;
5-nonyl-2-[4-(7-cyclopentyl-heptyloxy)-3-fluoro-phenyl]-pyrimidine;
5-nonyl-2-[4-(7-cyclopentyl-heptyloxy)-2-fluoro-phenyl]-pyrimidine;
5-heptyl-2-[4-(7-cyclopentyl-heptyloxy)-2,3-difluoro-phenyl]-pyrimidine;
5-octyl-2-[4-(7-cyclopentyl-heptyloxy)-2,3-difluoro-phenyl]-pyrimidine;
5-nonyl-2-[4-(7-cyclopentyl-heptyloxy)-2,3-difluoro-phenyl]-pyrimidine;
5-decyl-2-[4-(7-cyclopentyl-heptyloxy)-2,3-difluoro-phenyl]-pyrimidine;
5-(7-cyclopentyl-heptyloxy)-2-(4-octyl-phenyl)-pyrimidine;
5-(7-cyclopentyl-heptyloxy)-2-(4-nonyl-phenyl)-pyrimidine;
5-(7-cyclopentyl-heptyloxy)-2-(4-decyl-phenyl)-pyrimidine;
5-(8-cyclopentyl-octyloxy)-2-(4-heptyl-phenyl)-pyrimidine;
5-(8-cyclopentyl-octyloxy)-2-(4-octyl-phenyl)-pyrimidine;
5-(8-cyclopentyl-octyloxy)-2-(4-nonyl-phenyl)-pyrimidine;
5-(8-cyclopentyl-octyloxy)-2-(4-decyl-phenyl)-pyrimidine;
5-(9-cyclopentyl-nonyloxy)-2-(4-octyl-phenyl)-pyrimidine;
5-(9-cyclopentyl-nonyloxy)-2-(4-nonyl-phenyl)-pyrimidine;
5-hexyloxy-2-[4-(8-cyclopentyl-octyloxy)-phenyl]-pyrimidine;
5-heptyloxy-2-[4-(8-cyclopentyl-octyloxy)-phenyl]-pyrimidine;
5-octyloxy-2-[4-(8-cyclopentyl-octyloxy)-phenyl]-pyrimidine;
5-nonyloxy-2-[4-(8-cyclopentyl-octyloxy)-phenyl]-pyrimidine, m.p. (C-$S_C$) 66.5° C., $S_C$-$S_A$ 89.4° C., cl.p. ($S_A$-I) 91.5° C.;
5-decyloxy-2-[4-(8-cyclopentyl-octyloxy)-phenyl]-pyrimidine, m.p. (C-$S_C$) 64.1° C., cl.p. ($S_C$-I) 94.5° C.;
5-heptyloxy-2-[4-(7-cyclopentyl-heptyloxy)-phenyl]-pyrimidine;
5-octyloxy-2-[4-(7-cyclopentyl-heptyloxy)-phenyl]-pyrimidine, m.p. (C-$S_C$) 65.5° C., $S_C$-$S_A$ 88.1° C., $S_A$-N 93.3° C., cl.p. (N-I) 94.4° C.;
5-nonyloxy-2-[4-(7-cyclopentyl-heptyloxy)-phenyl]-pyrimidine, m.p. (C-$S_C$) 65.7° C., $S_C$-$S_A$ 93.2° C., cl.p. ($S_A$-I) 94.6° C.;
5-decyloxy-2-[4-(7-cyclopentyl-heptyloxy)-phenyl]-pyrimidine, m.p. (C-$S_C$) 65.1° C., cl.p. ($S_C$-I) 97.7° C.;

5-oct-2E-enyloxy-2-[4-(7-cyclopentyl-heptyloxy)-phenyl]-pyrimidine;
5-oct-4E-enyloxy-2-[4-(7-cyclopentyl-heptyloxy)-phenyl]-pyrimidine;
5-oct-5Z-enyloxy-2-[4-(7-cyclopentyl-heptyloxy)-phenyl]-pyrimidine;
5-(4-methyl-octyloxy-2-[4-(7-cyclopentyl-heptyloxy)-phenyl]-pyrimidine;
5-(5-methyl-octyloxy-2-[4-(7-cyclopentyl-heptyloxy)-phenyl]-pyrimidine;
5-(6-methyl-octyloxy-2-[4-(7-cyclopentyl-heptyloxy)-phenyl]-pyrimidine;
5-(7-cyclopentyl-heptyloxy)-2-[4-(7-cyclopentyl-heptyloxy)-phenyl]-pyrimidine;
5-(8-cyclopentyl-octyloxy)-2-[4-(8-cyclopentyl-octyloxy)-phenyl]-pyrimidine; m.p. (C-$S_C$) 87.4° C., cl.p. ($S_C$-I) 88.4° C.;
5-(7-cyclopentyl-heptyloxy)-2-(4-heptyloxy-phenyl)-pyrimidine;
5-(7-cyclopentyl-heptyloxy)-2-(4-octyloxy-phenyl)-pyrimidine, m.p. (C-$S_C$) 65.2° C., cl.p. ($S_C$-I) 98.2° C.;
5-(7-cyclopentyl-heptyloxy)-2-(4-nonyloxy-phenyl)-pyrimidine;
5-(7-cyclopentyl-heptyloxy)-2-(4-decyloxy-phenyl)-pyrimidine;
5-(8-cyclopentyl-octyloxy)-2-(4-hexyloxy-phenyl)-pyrimidine;
5-(8-cyclopentyl-octyloxy)-2-(4-heptyloxy-phenyl)-pyrimidine;
5-(8-cyclopentyl-octyloxy)-2-(4-octyloxy-phenyl)-pyrimidine;
5-(8-cyclopentyl-octyloxy)-2-(4-nonyloxy-phenyl)-pyrimidine;
(R)-5-(6-cyclopentyl-hexyloxy)-2-[4-(2-fluoro-octyloxy)-phenyl]-pyrimidine;
(R)-5-(7-cyclopentyl-heptyloxy)-2-[4-(2-fluoro-octyloxy)-phenyl]-pyrimidine;
(R)-5-(8-cyclopentyl-octyloxy)-2-[4-(2-fluoro-octyloxy)-phenyl]-pyrimidine;
(R)-5-(9-cyclopentyl-nonyloxy)-2-[4-(2-fluoro-octyloxy)-phenyl]-pyrimidine;
(R)-5-(10-cyclopentyl-decyloxy)-2-[4-(2-fluoro-octyloxy)-phenyl]-pyrimidine;
(S)-5-(7-cyclopentyl-heptyloxy)-2-[4-(3-fluoro-octyloxy)-phenyl]-pyrimidine;
(S,S)-5-(7-cyclopentyl-heptyloxy)-2-[4-(2,3-difluoro-octyloxy)-phenyl]-pyrimidine;
(S,S)-5-(7-cyclopentyl-heptyloxy)-2-[4-(2,3-epoxy-nonyloxy)-phenyl]-pyrimidine;
(S,S)-5-(8-cyclopentyl-octyloxy)-2-[4-(2,3-epoxy-nonyloxy)-phenyl]-pyrimidine;
(R)-5-(7-cyclopentyl-heptyloxy)-2-[4-(2-chloro-octyloxy)-phenyl]-pyrimidine;
(S)-5-(7-cyclopentyl-heptyloxy)-2-[4-(3-chloro-octyloxy)-phenyl]-pyrimidine;
5-octyl-2-[4-(7-cyclopentyl-heptyloxy)-2-fluoro-phenyl]-pyrimidine;
5-nonyl-2-[4-(7-cyclopentyl-heptyloxy)-2-fluoro-phenyl]-pyrimidine;
5-heptyl-2-[4-(7-cyclopentyl-heptyloxy)-3-fluoro-phenyl]-pyrimidine;
5-octyl-2-[4-(7-cyclopentyl-heptyloxy)-3-fluoro-phenyl]-pyrimidine;
5-nonyl-2-[4-(7-cyclopentyl-heptyloxy)-3-fluoro-phenyl]-pyrimidine;
5-heptyl-2-[4-(7-cyclopentyl-heptyloxy)-2,3-difluoro-phenyl]-pyrimidine;
5-octyl-2-[4-(7-cyclopentyl-heptyloxy)-2,3-difluoro-phenyl]-pyrimidine;
5-nonyl-2-[4-(7-cyclopentyl-heptyloxy)-2,3-difluoro-phenyl]-pyrimidine;
5-decyl-2-[4-(7-cyclopentyl-heptyloxy)-2,3-difluoro-phenyl]-pyrimidine;
5-heptyloxy-2-[4-(7-cyclopentyl-heptyloxy)-2-fluoro-phenyl]-pyrimidine;
5-heptyloxy-2-[4-(7-cyclopentyl-heptyloxy)-2,3-difluoro-phenyl]-pyrimidine;
5-octyloxy-2-[4-(7-cyclopentyl-heptyloxy)-2,3-difluoro-phenyl]-pyrimidine;
5-nonyloxy-2-[4-(7-cyclopentyl-heptyloxy)-2,3-difluoro-phenyl]-pyrimidine;
5-(7-cyclopentyl-heptyloxy)-2-(2,3-difluoro-4-octyl-phenyl)-pyrimidine;
5-(7-cyclopentyl-heptyloxy)-2-(2,3-difluoro-4-nonyl-phenyl)-pyrimidine;
(R)-5-(7-cyclopentyl-heptyloxy)-2-[2-fluoro-4-(2-fluoro-octyloxy)-phenyl]-pyrimidine;
(R)-5-(7-cyclopentyl-heptyloxy)-2-[3-fluoro-4-(2-fluoro-octyloxy)-phenyl]-pyrimidine;
(R)-5-(5-cyclopentyl-pentyloxy)-2-[2,3-difluoro-4-(2-fluoro-octyloxy)-phenyl]-pyrimidine;
(R)-5-(6-cyclopentyl-hexyloxy)-2-[2,3-difluoro-4-(2-fluoro-octyloxy)-phenyl]-pyrimidine;
(R)-5-(7-cyclopentyl-heptyloxy)-2-[2,3-difluoro-4-(2-fluoro-octyloxy)-phenyl]-pyrimidine;
(R)-5-(7-cyclopentyl-heptyloxy)-2-[2,3-difluoro-4-(2-fluoro-octyloxy)-phenyl]-pyrimidine;
4-[5-(7-cyclopentyl-heptyloxy)-pyrimidine-2-yl]-phenyl (R)-2-fluoro-octanoate;
4-[5-(7-cyclopentyl-heptyloxy)-pyrimidine-2-yl]-phenyl (R)-2-chloro-octanoate;
4-[5-(7-cyclopentyl-heptyloxy)-pyrimidine-2-yl]-phenyl (S)-2-cyano-octanoate;
4-[5-(7-cyclopentyl-heptyloxy)-pyrimidine-2-yl]-phenyl-(S)-2-methyl-octanoate;
4-[5-(7-cyclopentyl-heptyloxy)-pyrimidine-2-yl]-phenyl (R)-2-(trifluoromethyl)-octanoate;
4-[5-(7-cyclopentyl-heptyloxy)-pyrimidine-2-yl]-phenyl (R)-2-fluoro-2-methyl-octanoate;
4-[5-(8-cyclopentyl-octyloxy)-pyrimidine-2-yl]-phenyl (2R, 3S)-2,3-epoxy-octanoate;
5-nonyloxy-2-[4-(8-cyclopentyl-octyloxy)-phenyl]-pyrazine;
4-nonyloxy-4'-(8-cyclopentyl-octyloxy)-tolane;
4,4'-bis(7-cyclopentyl-heptyloxy)-tolane;
4,4'-bis(8-cyclopentyl-octyloxy)-tolane;
4-(8-cyclopentyl-octyloxy)-phenyl 4-nonyl-benzoate;
4-(8-cyclopentyl-octyloxy)-phenyl 4-decyloxy-benzoate;
3-fluoro-4-(8-cyclopentyl-octyloxy)-phenyl 4-decyloxybenzoate;
4"-heptyl-4-(4-cyclopentyl-butyloxy)-2'-fluoro-[1,1';4'-1"]terphenyl;
4"-heptyl-4-(4-cyclopentyl-butyloxy)-3-fluoro-[1,1';4'-1']terphenyl;
4"-hexyl-4-(4-cyclopentyl-butyloxy)-2",3"-difluoro-[1,1';4'-1"]terphenyl;
4"-heptyl-4-(4-cyclopentyl-butyloxy)-2,3-difluoro-[1,1';4'-1"]terphenyl;
4"-heptyl-4-(5-cyclopentyl-pentyloxy)-2'-fluoro-[1,1';4'-1"]terphenyl;
4"-heptyl-4-(5-cyclopentyl-pentyloxy)-3-fluoro-[1,1';4'-1"]terphenyl;
4"-hexyl-4-(5-cyclopentyl-pentyloxy)-2",3"-difluoro-[1,1';4'-1"]terphenyl;

4"-heptyl-4-(5-cyclopentyl-pentyloxy)-2,3-difluoro-[1,1';4'-1"]terphenyl;

4"-hexyl-4-(5-cyclopentyl-pentyloxy)-3,2"-difluoro-[1,1';4'-1"]terphenyl;

trans-5-octyl-2-[4'-(5-cyclopentyl-pentyloxy)-biphenyl-4-yl]-1,3-dioxane;

trans-5-nonyl-2-[4'-(5-cyclopentyl-pentyloxy)-biphenyl-4-yl]-1,3-dioxane;

trans-5-octyl-2-[4'-(5-cyclopentyl-pentyloxy)-3'-fluoro-biphenyl-4-yl]-1,3-dioxane;

trans-5-nonyl-2-[4'-(5-cyclopentyl-pentyloxy)-3'-fluoro-biphenyl-4-yl]-1,3-dioxane;

4-(trans-5-octyl-1,3-dioxan-2-yl)-phenyl 4-(6-cyclopentylhexyloxy)-benzoate;

4-(trans-5-octyl-1,3-dioxan-2-yl)-phenyl 3-fluoro-4-(6-cyclopentyl-hexyloxy)-benzoate;

4-(trans-5-nonyl-1,3-dioxan-2-yl)-phenyl 3-fluoro-4-(6-cyclopentyl-hexyloxy)-benzoate;

4-(trans-5-nonyl-1,3-dioxan-2-yl)-phenyl 2,3-difluoro-4-(6-cyclopentyl-hexyloxy)-benzoate;

4-(trans-5-nonyl-1,3-dioxan-2-yl)-phenyl 2,3-difluoro-4-(7-cyclopentyl-heptyloxy)-benzoate;

trans-5-nonyl-2-[2',3'-difluoro-4'-(7-cyclopentyl-heptyloxy)-biphenyl-4-yl]-1,3-dioxane;

5-(trans-5-octyl-1,3-dioxan-2-yl)-[2-(3-fluoro-4-(6-cyclopentyl-hexyloxy)-phenyl]-pyridine;

5-(trans-5-nonyl-1,3-dioxan-2-yl)-[2-(2,3-difluoro-4-(7-cyclopentyl-heptyloxy)-phenyl]-pyridine;

4'-[5-(5-cyclopentyl-pentyloxy)-pyrimidine-2-yl]-phenyl trans-4-hexyl-cyclohexanecarboxylate;

4'-[5-(5-cyclopentyl-pentyloxy)-pyrimidine-2-yl]-phenyl trans-4-pentyl-cyclohexanecarboxylate;

5-(5-cyclopentyl-pentyloxy)-2[4-[2-(trans-4-hexyl-cyclohexyl)-ethyl]-phenyl]-pyrimidine;

5-(5-cyclopentyl-pentyloxy)-2[[2-(trans-4-hexyl-cyclohexyl)methoxy]-phenyl]-pyrimidine;

5-(5-cyclopentyl-pentyloxy)-2-[4-(trans-4-hexyl-cyclohexyl)-phenyl]-pyrimidine;

5-(7-cyclopentyl-heptyloxy)-2-[4'-pentyl-biphenyl-4-yl]-pyrimidine;

5-(8-cyclopentyl-octyloxy)-2-[4'-pentyl-biphenyl-4-yl]-pyrimidine;

5-(7-cyclopentyl-heptyloxy)-2-[4'-hexyl-biphenyl-4-yl]-pyrimidine;

5-(4-cyclopentyl-butyloxy)-2-[4'-hexyl-biphenyl-4-yl]-pyrimidine;

5-(6-cyclopentyl-hexyloxy)-2-[4'-hexyl-biphenyl-4-yl]-pyrimidine;

5-(7-cyclopentyl-heptyloxy)-2-[4'-hexyl-biphenyl-4-yl]-pyrimidine;

5-(8-cyclopentyl-octyloxy)-2-[4'-hexyl-biphenyl-4-yl]-pyrimidine, m.p. (C-S$_C$) 119.0° C., S$_C$-N 157.0° C., cl.p. (N-I) 162.5° C.;

5-(6-cyclopentyl-hexyloxy)-2-[4'-heptyl-biphenyl-4-yl]-pyrimidine;

5-(7-cyclopentyl-heptyloxy)-2-[4'-heptyl-biphenyl-4-yl]-pyrimidine;

5-heptyl-2-[4'-(6-cyclopentyl-hexyloxy)-biphenyl-4-yl]-pyrimidine;

5-heptyl-2-[4'-(7-cyclopentyl-heptyloxy)-biphenyl-4-yl]-pyrimidine;

5-(7-cyclopentyl-heptyloxy)-2-[4'-pentyl-biphenyl-4-yl]-pyrimidine;

5-(8-cyclopentyl-octyloxy)-2-[4'-pentyl-biphenyl-4-yl]-pyrimidine;

2-(7-cyclopentyl-heptyloxy)-5-[4'-hexyl-biphenyl-4-yl]-pyrimidine;

2-(4-cyclopentyl-butyloxy)-5-[4'-hexyl-biphenyl-4-yl]-pyrimidine;

2-(6-cyclopentyl-hexyloxy)-5-[4'-hexyl-biphenyl-4-yl]-pyrimidine;

2-(7-cyclopentyl-heptyloxy)-5-[4'-hexyl-biphenyl-4-yl]-pyrimidine;

2-(8-cyclopentyl-octyloxy)-5-[4'-hexyl-biphenyl-4-yl]-pyrimidine;

2-(6-cyclopentyl-hexyloxy)-5-[4'-heptyl-biphenyl-4-yl]-pyrimidine;

2-(7-cyclopentyl-heptyloxy)-5-[4'-heptyl-biphenyl-4-yl]-pyrimidine;

2-heptyl-5-[4'-(6-cyclopentyl-hexyloxy)-biphenyl-4-yl]-pyrimidine;

2-heptyl-5-[4'-(7-cyclopentyl-heptyloxy)-biphenyl-4-yl]-pyrimidine;

2-(4-hexyl-phenyl)-5-[4-(7-cyclopentyl-heptyloxy)-phenyl]-pyrimidine;

2-(4-heptyl-phenyl)-5-[4-(7-cyclopentyl-heptyloxy)-phenyl]-pyrimidine;

4-[2-[4-(7-cyclopentyl-heptyloxy)-phenyl]-pyrimidine-5-yl]-phenyl (R)-2-fluoro-octanoate;

4-[2-[4-(7-cyclopentyl-heptyloxy)-phenyl]-pyrimidine-5-yl]-phenyl (R)-2-methyl-octanoate;

4-[2-[4-(7-cyclopentyl-heptyloxy)-phenyl]-pyrimidine-5-yl]-phenyl (R)-2-fluoro-2-methyl-octanoate;

5-heptyl-2-[6-(7-cyclopentyl-heptyloxy)-naphth-2-yl]-pyrimidine;

5-octyl-2-[6-(7-cyclopentyl-heptyloxy)-naphth-2-yl]-pyrimidine;

5-nonyl-2-[6-(7-cyclopentyl-heptyloxy)-naphth-2-yl]-pyrimidine;

6-octyl-2-[4-(7-cyclopentyl-heptyloxy)-phenyl]-quinoline;
6-nonyl-2-[4-(7-cyclopentyl-heptyloxy)-phenyl]-quinoline;

2-(4-hexyl-phenyl)-5-[4-(5-cyclopentyl-pentyloxy)-phenyl]-1,3,4-thiadiazole;

2-(4-hexyl-phenyl)-5-[4-(5-cyclopentyl-pentyloxy)-phenyl]-thiazole;

5-(4-hexyl-phenyl)-2-[4-(5-cyclopentyl-pentyloxy)-phenyl]-thiazole;

2-(4-hexyl-phenyl)-5-[4-(5-cyclopentyl-pentyloxy)-phenyl]-thiophene;

4-heptyl-phenyl 4'-(7-cyclopentyl-heptyloxy)-biphenyl-4-carboxylate;

(S)-4-[1-(pentyloxy-carbonyl)-ethyl]-phenyl 4'-(7-cyclopentylheptyloxy)-biphenyl-4-carboxylate.

EXAMPLE 2

A solution of 1.86 g of 5-(9-cyclopentyl-non-1-enyl)-2-(4-heptyloxy-phenyl)-pyrimidine in 35 ml of toluene is hydrogenated with 0.24 g of 5% palladium/charcoal at room temperature and normal pressure until the hydrogen uptake comes to a standstill. Recrystallization from ethanol of the crude product obtained after filtration and concentration of the filtrate yields pure 5-(9-cyclopentyl-nonyl)-2-(4-heptyloxy-phenyl)-pyrimidine.

The 5-(9-cyclopentyl-non-1-enyl)-2-(4-heptyloxy-phenyl)-pyrimidine used as the starting material can be prepared as follows:

a) 11 ml of a 20% (v/v) diisobutylaluminium hydride solution in toluene are added dropwise in a nitrogen atmosphere at 0° to 5° C. within 15 minutes to a solution of 2.09 g of 2-(4-heptyloxyphenyl)-pyrimidine-5-carbonitrile in 40 ml of toluene. The reaction mixture is stirred at 0° C. for a further 2 hours and poured into 100 ml of ice-cold 1N hydrochloric acid. After completion of the reaction the phases are separated. The organic phase is washed neutral with water, dried over sodium sulfate, filtered and the filtrate is concentrated. 2-(4-Heptyloxy-phenyl)-pyrimidine-5-carboxaldehyde is obtained.

b) A suspension of 3.7 g of (8-cyclopentyl-octyl)-triphenylphosphonium bromide (prepared by heating 3.4 g of (8-bromooctyl)-cyclopentane and 3.9 g of triphenylphosphine in 15 ml of toluene overnight and precipitation of the product from the cooled reaction mixture by addition of hexane) in 20 ml of tert.-butyl methyl ether is treated with 0.8 g of potassium tert.-butylate and the yellow suspension is stirred at room temperature for 45 minutes. Then, a solution of 1.64 g of 2-(4-heptyloxy-phenyl)-pyrimidine-5-carboxaldehyde in 10 ml of tetrahydrofuran is added dropwise at 0° to 5° C. The reaction mixture is stirred at 0° C. for a further 2 hours and then triturated with 10 ml of saturated sodium hydrogen carbonate solution. The phases are separated and the organic phase is washed with saturated sodium chloride solution, dried over sodium sulphate, filtered and concentrated. The residue is partitioned between methanol/water (vol.) 4:1 and hexane and the methanol phase is separated. The hexane phase is washed with methanol/water 4:1 and the filtrate is concentrated. The crude 5-(9-cyclopentyl-non-1-enyl)-2-(4-heptyloxy-phenyl)-pyrimidine obtained is purified by chromatography on 10 g of silica gel with hexane/ethyl acetate 19:1 (v/v).

The following compounds can be prepared analogously:

5-(8-Cyclopentyl-octyl)-2-(4-heptyloxy-phenyl)-pyrimidine;
5-(8-cyclopentyl-octyl)-2-(4-octyloxy-phenyl)-pyrimidine;
5-(8-cyclopentyl-octyl)-2-(4-oct-2E-enyloxy-phenyl)-pyrimidine;
5-(8-cyclopentyl-octyl)-2-(4-oct-3Z-enyloxy-phenyl)-pyrimidine;
5-(8-cyclopentyl-octyl)-2-(4-oct-5Z-enyloxy-phenyl)-pyrimidine;
(R)-5-(6-cyclopentyl-hexyl)-2-[4-(2-fluoro-octyloxy)-phenyl]-pyrimidine;
(R)-5-(7-cyclopentyl-heptyl)-2-[4-(2-fluoro-octyloxy)-phenyl]-pyrimidine;
(R)-5-(8-cyclopentyl-octyl)-2-[4-(2-fluoro-octyloxy)-phenyl]-pyrimidine;
(R)-5-(9-cyclopentyl-nonyl)-2-[4-(2-fluoro-octyloxy)-phenyl]-pyrimidine;
(R)-5-(10-cyclopentyl-decyl)-2-[4-(2-fluoro-octyloxy)-phenyl]-pyrimidine;
(R)-5-(8-cyclopentyl-octyl)-2-[3-fluoro-4-(2-fluoro-octyloxy)-phenyl]-pyrimidine;
(R)-5-(6-cyclopentyl-hexyl)-2-[2,3-difluoro-4-(2-fluoro-octyloxy)-phenyl]-pyrimidine;
(R)-5-(7-cyclopentyl-heptyl)-2-[2,3-difluoro-4-(2-fluoro-octyloxy)-phenyl]-pyrimidine;
(R)-5-(8-cyclopentyl-octyl)-2-[2,3-difluoro-4-(2-fluoro-octyloxy)-phenyl]-pyrimidine;
(R)-5-(9-cyclopentyl-nonyl)-2-[2,3-difluoro-4-(2-fluoro-octyloxy)-phenyl]-pyrimidine;
(S)-5-(7-cyclopentyl-heptyl)-2-[4-(3-fluoro-octyloxy)-phenyl]-pyrimidine;
(S)-5-(8-cyclopentyl-octyl)-2-[4-(3-fluoro-octyloxy)-phenyl]-pyrimidine;
(S,S)-5-(7-cyclopentyl-heptyl)-2-[4-(2,3-difluoro-octyloxy)-phenyl]-pyrimidine;
(S,S)-5-(8-cyclopentyl-octyl)-2-[4-(2,3-difluoro-octyloxy)-phenyl]-pyrimidine;
(S)-5-(8-cyclopentyl-octyl)-2-[4-(3-fluoro-octyloxy)-phenyl]-pyrimidine;
(R,R)-5-(8-cyclopentyl-octyl)-2-[4-(2,3-epoxy-nonyloxy)-phenyl]-pyrimidine;
(R,R)-5-(9-cyclopentyl-nonyl)-2-[4-(2,3-epoxy-nonyloxy)-phenyl]-pyrimidine;
5-(8-cyclopentyl-octyl)-2-(4-octyloxy-phenyl)-pyrimidine;
5-(6-cyclopentyl-hexyl)-2-(4-heptyloxy-phenyl)-pyridine;
5-(8-cyclopentyl-octyl)-2-(4-heptyloxy-phenyl)-pyridine;
(R)-5-(8-cyclopentyl-octyl)-2-[4-(2-fluoro-octyloxy)-phenyl]-pyridine;
5-(8-cyclopentyl-octyl)-2-(4-heptyloxy-phenyl)-pyrazine;
4-[5-(8-cyclopentyl-octyl)-pyrimidin-2-yl]-phenyl (R)-2-fluoro-octanoate;
4-[5-(8-cyclopentyl-octyl)-pyrimidin-2-yl]-phenyl (R)-2-chloro-octanoate;
4-[5-(8-cyclopentyl-octyl)-pyrimidin-2-yl]-phenyl (S)-2-cyano-octanoate;
4-[5-(8-cyclopentyl-octyl)-pyrimidin-2-yl]-phenyl (S)-2-methyl-octanoate;
4-[5-(8-cyclopentyl-octyl)-pyrimidin-2-yl]-phenyl (R)-2-(trifluoromethyl)-octanoate;
4-[5-(8-cyclopentyl-octyl)-pyrimidin-2-yl]-phenyl (R)-2-fluoro-2-methyl-octanoate;
4-[5-(8-cyclopentyl-octyl)-pyrimidin-2-yl]-phenyl (2R,3S)-2,3-epoxy-octanoate;
4-[5-[4-(6-cyclopentyl-hexyl)-phenyl]-pyrimidin-2-yl]-phenyl (S)-2-chloro-3-methyl-butanoate;
4-[5-[4-(6-cyclopentyl-hexyl)-phenyl]-pyrimidin-2-yl]-phenyl (S,S)-2-chloro-3-methyl-pentanoate;
(S)-oct-2-yl 4-[5-[4-(6-cyclopentyl-hexyl)-phenyl]-pyrimidin-2-yl]-benzoate;
(R)-1-(trifluoromethyl)-heptyl 4-[5-[4-(6-cyclopentyl-hexyl)-phenyl]-pyrimidin-2-yl]-benzoate;
(S)-2-butyloxy-propyl 4-[5-[4-(6-cyclopentyl-hexyl)-phenyl]-pyrimidin-2-yl]-benzoate;
(S)-2-pentyloxy-propyl 4-[5-[4-(6-cyclopentyl-hexyl)-phenyl]-pyrimidin-2-yl]-benzoate;
(S)-5-[4-(6-cyclopentyl-hexyl)-phenyl]-2-(4-oct-2-yloxyphenyl)-pyrimidine;
pentyl (S)-2-[4-[5-[4-(6-cyclopentyl-hexyl)-phenyl]pyrimidin-2-yl]-phenoxy]-propionate.

EXAMPLE 3

A solution of 0.24 g of N,N'-dicyclohexyl-carbodiimide in 5 ml of dichloromethane is added dropwise at 0° C. within 15 minutes to a solution of 0.125 g of cyclopentanenonanoic acid, 0.142 g of 4-(5-octyl-pyrimidin-2-yl)-phenol and 0.015 g of 4-dimethylaminopyridine in 10 ml of dichloromethane. The suspension is stirred at 0° C. for a further 30 minutes, filtered and the filtrate is concentrated. The residue is chromatographed on 10 g of silica gel with hexane/ethyl acetate 19:1 (v/v). Recrystallization of the product-containing fractions from ethanol yields pure 4-(5-octylpyrimidin-2-yl)-phenyl-cyclopentane-nonanoate.

The following compounds can be prepared analogously:
4-(5-Octyl-pyrimidin-2-yl)-phenylcyclopentaneoctanoate;
4-(5-nonyl-pyrimidin-2-yl)-phenyl cyclopentaneheptanoate;
4-(5-nonyl-pyrimidin-2-yl)-phenyl cyclopentaneoctanoate;
4-(5-nonyl-pyrimidin-2-yl)-phenyl cyclopentanenonanoate;
(R)-4-[5-(2-fluoro-octyl)-pyrimidin-2-yl]-phenyl cyclopentanenonanoate;
4-(5-heptyl-pyridin-2-yl)-phenyl cyclopentaneheptanoate;
4-(5-octyl-pyridin-2-yl)-phenyl cyclopentaneoctanoate;
4-(5-nonyl-pyridin-2-yl)-phenyl cyclopentaneheptanoate;
4'-(5-nonyl-pyridin-2-yl)-biphenyl-4-yl cyclopentanehexanoate;
4'-(5-octyl-pyridin-2-yl)-biphenyl-4-yl cyclopentaneoctanoate;
4'-(5-decyl-pyridin-2-yl)-biphenyl-4-yl cyclopentaneoctanoate;

4'-(5-hexyl-pyrimidin-2-yl)-biphenyl-4-yl cyclopentanehexanoate;

4'-(5-pentyl-pyrimidin-2-yl)-biphenyl-4-yl cyclopentaneoctanoate;

4'-(5-hexyl-pyrimidin-2-yl)-biphenyl-4-yl cyclopentaneoctanoate;

4'-(5-heptyl-pyrimidin-2-yl)-biphenyl-4-yl cyclopentaneoctanoate;

4'-(5-pentyl-pyrimidin-2-yl)-biphenyl-4-yl cyclopentanenonanoate;

4'-(5-hexyl-pyrimidin-2-yl)-biphenyl-4-yl cyclopentanenonanoate;

4'-(5-heptyl-pyrimidin-2-yl)-biphenyl-4-yl cyclopentanenonanoate;

4'-(5-pentyl-pyrimidin-2-yl)-biphenyl-4-yl cyclopentanedecanoate;

2-(4'-pentyl-biphenyl-4-yl)-pyrimidin-5-yl cyclopentaneheptanoate;

2-(4'-hexyl-biphenyl-4-yl)-pyrimidin-5-yl cyclopentanehexanoate;

2-(4'-hexyl-biphenyl-4-yl)-pyrimidin-5-yl cyclopentaneheptanoate;

2-(4'-heptyl-biphenyl-4-yl)-pyrimidin-5-yl cyclopentanehexanoate, 2-(4'-heptyl-biphenyl-4-yl)-pyrimidin-5-yl cyclopentaneheptanoate;

2-(4'-pentyl-biphenyl-4-yl)-pyrimidin-5-yl cyclopentaneoctanoate;

2(4'-hexyl-biphenyl-4-yl)-pyrimidin-5-yl cyclopentaneoctanoate;

2-(4'-heptyl-biphenyl-4-yl)-pyrimidin-5-yl cyclopentaneoctanoate;

2-(4'-pentyl-biphenyl-4-yl)-pyrimidin-5-yl cyclopentanenonanoate;

2-(4'-hexyl-biphenyl-4-yl)-pyrimidin-5-yl cyclopentanenonanoate;

(R)-2-[4'-(2-fluoro-octyl)-biphenyl-4-yl]-pyrimidin-2-yl) cyclopentanenonanoate;

(S)-2-[4'-(3-fluorononyl}-biphenyl-4-yl]-pyrimidin-2-yl) cyclopentanenonanoate;

4-[[4-(trans-4-heptyl-cyclohexyl)-phenyl]-ethynyl]-phenyl cyclopentaneheptanoate;

4"-heptyl-2'-fluoro-[1,1';4'-1"]terphenyl-4-yl cyclopentaneheptanoate;

4"-heptyl-3-fluoro-[1,1';4'-1"]terphenyl-4-yl cyclopentanehexanoate;

4"-hexyl-2",3"-difluoro-[1,1';4'-1"]terphenyl-4-yl cyclopentaneoctanoate;

4"-heptyl-2,3-difluoro-[1,1';4'-1"]terphenyl-4-yl cyclopentaneheptanoate;

4"-hexyl-3,2"-difluoro-[1,1';4'-1"]terphenyl-4-yl cyclopentaneoctanoate.

EXAMPLE 4

A solution of 0.3 g of N,N'-dicyclohexyl-carbodiimide in 6 ml of dichloromethane is added dropwise at 0° C. within 15 minutes to a solution of 0.201 g of 4-(5-octyl-pyrimidin-2-yl)-benzoic acid, 0.116 g of cyclopentane-hexanol and 0.02 g of 4-dimethylaminopyridine in 10 ml of dichloromethane. The suspension is stirred at 0° C. for a further 1 hour, filtered and concentrated. The residue is chromatographed on 10 g of silica gel with hexane/ethyl acetate 19:1 (v/v). Recrystallization of the product-containing fractions from ethanol gives pure 6-cyclopentyl-hexyl 4-(5-octyl-pyrimidin-2-yl)-benzoate.

The following compounds can be prepared analogously:
6-Cyclopentyl-hexyl 4-(5-nonyl-pyrimidin-2-yl)-benzoate;

7-cyclopentyl-heptyl 4-(5-octyl-pyrimidin-2-yl)-benzoate;
7-cyclopentyl-heptyl 4-(5-heptyl-pyrimidin-2-yl)-benzoate;
7-cyclopentyl-heptyl 4-(5-nonyl-pyrimidin-2-yl)-benzoate;
6-cyclopentyl-hexyl 4-(5-nonyl-pyrimidin-2-yl)-2-fluorobenzoate;
6-cyclopentyl-hexyl 4-(5-octyl-pyrimidin-2-yl)-2,3-difluorobenzoate;
6-cyclopentyl-hexyl 4-(5-hepyloxy-pyrimidin-2-yl)-benzoate;
6-cyclopentyl-hexyl 4-(5-nonyl-pyridin-2-yl)-benzoate;
7-cyclopentyl-heptyl 4-(5-octyl-pyridin-2-yl)-benzoate;
6-cyclopentyl-hexyl 4-(5-nonyl-pyrazin-2-yl)-benzoate;
7-cyclopentyl-heptyl 4-(5-octyl-pyrazin-2-yl)-benzoate;
8-cyclopentyl-octyl 4-(4-nonyl-benzoyloxy)-benzoate;
8-cyclopentyl-octyl 4-(4-octyloxy-benzoyloxy)-benzoate.

EXAMPLE 5

In order to investigate the properties of compounds of formula I, 15 wt. % of a compound of formula I or for comparative purposes 15 wt. % of an analogous compound without a cyclopentane ring were admixed with 85 wt. % of a basic mixture (BM). The phase sequence of these mixtures was determined and the spontaneous polarization $(P_s)$, the switching time $(\tau)$ and in some cases the switching angle $(2\theta)$ were measured. The measurements were carried out under the following conditions: $P_s$ at 8.5 µm cell thickness and a delta voltage of 10 Hz and 5 V/µm; switching times (to $I_{max}$) at 10 V/pp/µm square-wave voltage; switching angle at 2 µm cell thickness and a voltage of 25 V. All measurements were carried out at 25° C.

Basic Mixture (BM)

16.6 wt. % of trans-4-[4-(2,3-difluoro-4-octyloxybenzoyloxy)-phenyl]-cyclohexyl (R)-2-fluorohexanoate, 23.8 wt. % of 5-nonyl-2-(4-hexyloxy-phenyl)-pyrimidine, 23.4 wt. % of 5-nonyl-2-(4-nonyloxy-phenyl)-pyrimidine, 11.8 wt. % of 5-octyl-2-(4-nonyloxy-phenyl)-pyrimidine, 12.3 wt. % of 5-octyl-2-(4-decyloxy-phenyl)-pyrimidine, 12.1 wt. % of 5-heptyl-2-(4-heptyloxy-phenyl)-pyrimidine:

Phase sequence [°C.] I 74.6 N* 67.7 $S_A$ 60.6 $S_C$*.

Mixture 1

85 wt. % of BM 15 wt. % of 5-nonyl-2-[4-(7-cyclopentyl-heptyloxy)-phenyl]-pyrimidine:

Phase sequence I 74.6 N* 67.7 $S_A$ 60.6 $S_C$*; $P_s$ 15.8 nC/cm$^2$; τ 174 µs; 2θ 53.9°.

Comparative Mixture 1

85 wt. % of BM with 15 wt. % of 5-nonyl-2-(4-nonyloxy-phenyl)-pyrimidine:

Phase sequence I 71.0 N* 66.0 $S_A$ 60.0 $S_C$*; $P_s$ 16.0 nC/cm$^2$; τ 120 µs; 2θ 50.2°.

Mixture I leads, in contrast to Comparative Mixture I, which has otherwise similar physical data, to a longer switching time and at the same time to a clearly larger switching angle.

Mixture 2

85 wt. % of BM with 15 wt. % of 5-octyl-2-[4-(8-cyclopentyl-octyloxy)-phenyl]-pyrimidine:

Phase sequence: I: 72.2; N*: 64.4; $S_A$: 58.3; $S_C$*; $P_s$ 17.0 nC/cm$^2$; τ 150 µs.

Mixture 3

85 wt. % of BM with 15 wt. % of 5-nonyl-2-[4-(8-cyclopentyl-octyloxy)-phenyl]-pyrimidine:

Phase sequence I 72.5 N* 66.5 $S_A$ 58.9 $S_C$*; $P_s$ 15.5 nC/cm$^2$; τ 140 μs.

Mixture 4

85 wt. % of BM with 15 wt. % of 5-nonyloxy-2-[4-(7-cyclopentyl-heptyloxy)-phenyl]-pyrimidine:

Phase sequence I 76.9 N* 71.9 $S_A$ 63.5 $S_C$*; $P_s$ 16.5 nC/cm$^2$; τ 153 μs.

Mixture 5

85 wt. % of BM with 15 wt. % of 5-nonyloxy-2-[4-(8-cyclopentyl-octyloxy)-phenyl]-pyrimidine:

Phase sequence I 76.7 N* 70.6 $S_A$ 61.8 $S_C$*; $P_s$ 16.1 nC/cm$^2$; τ 150 μs.

Mixture 6

85 wt. % of BM with 15 wt. % of 5-decyloxy-2-[4-(8-cyclopentyl-octyloxy)-phenyl]-pyrimidine:

Phase sequence I 76.5 N* 71.1 $S_A$ 61.2 $S_C$*; $P_s$ 16.0 nC/cm$^2$; τ 132 μs.

Mixture 7

85 wt. % of BM with 15 wt. % of 5-(7-Cyclopentyl-heptyloxy)-2-(4-octyloxyphenyl)-pyrimidine:

Phase sequence I 77.7 N* 73.8 $S_A$ 65.9 $S_C$*; $P_s$ 16.6 nC/cm$^2$; τ 140 μs; 2θ 54°.

Comparative Mixture 2

85 wt. % of BM with 15 wt. % of 5-oct-7-enyloxy-2-(4-oct-7-enyloxy-phenyl)-pyrimidine:

Phase sequence I 74.7 N* 69.7 $S_A$ 58.2 $S_C$*; $P_s$ 14.8 nC/cm$^2$; τ 90 μs; 2θ 49.4°.

Mixture 7 leads to a longer switching time and at the same time to a clearly larger switching angle and to a clearly higher $S_C$* upper limit than Comparative Mixture 2.

Mixture 8

85 wt. % of BM with 15 wt. % of 5-(8-cyclopentyl-octyloxy)-2-[4-(8-cyclopentyloctyloxy)-phenyl]-pyrimidine:

Phase sequence I 75.5 N* 73.5 $S_A$ 60.9 $S_C$*; $P_s$ 15.8 nC/cm$^2$; τ 155 μs.

Mixture 9

85 wt. % of BM with 15 wt. % of 5-nonyl-2-[4-(7-cyclopentyl-heptyloxy)-phenyl]-pyridine:

Phase sequence I 73.0 N* 69.2 $S_A$ 63.4 $S_C$*; $P_s$ 17.1 nC/cm$^2$; τ 136 μs; 2θ 54.3°.

Comparative Mixture 3

85 wt. % of BM with 15 wt. % of 5-nonyl-2-(4-dec-9-enyloxy-phenyl)-pyridine:

Phase sequence I 73.4 N* 70.3 $S_A$ 61.6 $S_C$*; $P_s$ 16.1 nC/cm$^2$; τ 90 μs; 2θ 49.4°.

Mixture 9 leads to a longer switching time and at the same time to a clearly larger switching angle and to a somewhat higher $S_C$* upper limit than Comparative Mixture 3.

Mixture 10

85 wt. % of BM with 15 wt. % of 5-heptyl-2-[4-(8-cyclopentyl-octyloxy)-phenyl]-pyridine:

Phase sequence I 73.0 N* 69.5 $S_A$ 62.2 $S_C$*; $P_s$ 16.1 nC/cm$^2$; τ 130 μs.

Mixture 11

85 wt. % of BM with 15 wt. % of 5-nonyl-2-[4-(8-cyclopentyl-octyloxy)-phenyl]-pyridine:

Phase sequence I 72.1 N* 67.5 $S_A$ 61.7 $S_C$*; $P_s$ 16.9 nC/cm$^2$; τ 136 μs.

We claim:

1. A cyclopentyl compound of the formula

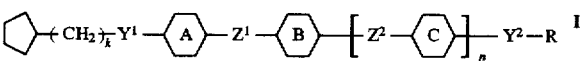

wherein k is a whole number of 4 to 18;

n is 0 or 1;

$Y^1, Y^2$ is a single bond, —O—, —COO— or —OOC—;

rings A, B, C each independently are 1,4-phenylene, pyrimidine-2,5-diyl, pyridine-2,5-diyl, pyrazine-2,5-diyl, naphthalene-2,6-diyl, quinoline-2,6-diyl, thiophene-2,5-diyl, thiazole-2,5-diyl or 1,3,4-thiadiazole-2,5-diyl, which are unsubstituted, mono or difluorinated, and ring C also is trans-1,4-cyclohexylene or trans-1,3-dioxane-2,5-diyl;

$Z^1$ is a single bond, —COO—, —OOC— or —C≡C—;

$Z^2$ is —COO—, —OOC—, —OCH$_2$—, —CH$_2$O— or —(CH$_2$)$_2$—; and

R is straight-chain or branched, optically inactive or optically active, alkyl or alkenyl with 4 to 20 carbon atoms in which one or two non-adjacent methylene groups can be replaced independently by —O—, —COO—, —OOC— or epoxyethylene, in which one or more hydrogen atoms can be replaced by fluorine, in which one hydrogen atom can be replaced by chlorine or cyano, and in which a terminal hydrogen atom can be replaced by cyclopentyl.

2. A compound in accordance with claim 1, wherein rings A, B and C each independently are 1,4-phenylene, 2- or 3-fluoro-1,4-phenylene, 2,3-difluoro-1,4-phenylene, pyrimidine-2,5-diyl, pyridine-2,5-diyl or pyrazine-2,5-diyl and ring C also signifies trans-1,4-cyclohexylene or trans-1,3-dioxane-2,5-diyl.

3. A compound according to claim 2, wherein at least one of rings A, B and C is 1,4-phenylene, 2- or 3-fluoro-1,4-phenylene or 2,3-difluoro-1,4-phenylene and a maximum of one of rings A, B and C is pyrimidine-2,5-diyl, pyridine-2,5-diyl or pyrazine-2,5-diyl.

4. A compound according to claim 1 of the formula

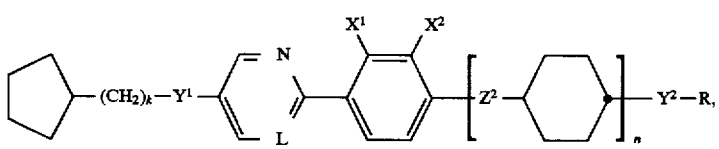

Ia

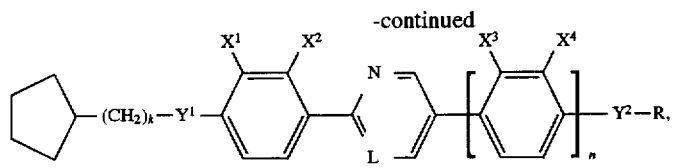

Ib

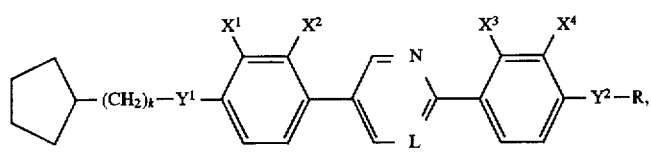

Ic

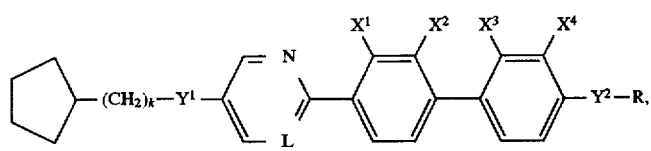

Id

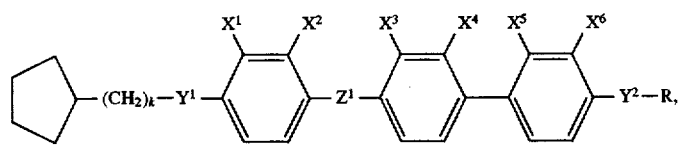

Ie

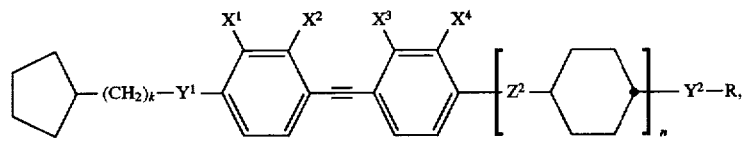

If

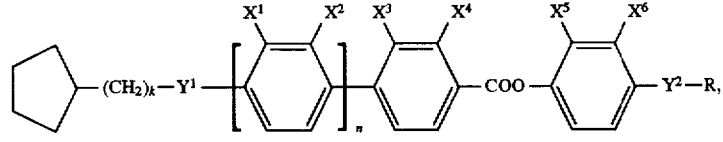

Ig

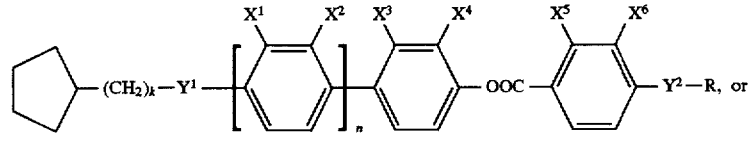

Ih

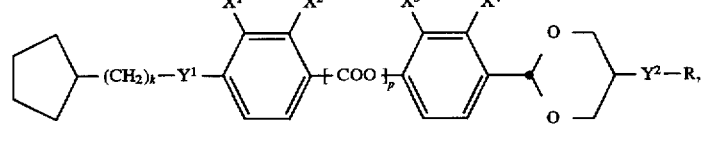

Ii wherein

L is nitrogen or —CH=;
$X^1$-$X^6$ are, independently, hydrogen or fluorine; and
p is 0 or 1.

5. A compound according to claim 4, wherein k is a whole number of 5 to 12.

6. A compound according to claim 5, wherein $Y^1$ is a single bond, —O— or —COO—.

7. A compound according to claim 6, wherein $Y^1$ is —O—.

8. A compound according to claim 7, wherein R is an alkyl or alkenyl residue with 5 to 12 carbon atoms in which 1 or 2 non-terminal methylene groups are replaced independently by —C*H(W)—, —C*F(CH$_3$)— or epoxyethylene, and in which 1 or 2 non-adjacent methylene groups can be replaced independently by —O—, —COO—, —OOC—; wherein W is fluorine, chlorine, cyano, methyl or trifluoromethyl and C* is a chiral centre.

9. A compound according to claim 8, wherein —$Y^2$—R is an optically active group.

10. A compound according to claim 9, wherein —$Y^2$—R is 2- or 3-fluoroalkyl, 2- or 3-fluoroalkoxy, 2,3-difluoroalkoxy, 2- or 3-fluoro-alkanoyloxy, 2,3-difluoro-alkanoyloxy, 2-fluoro-2-methylalkanoyloxy, 2-fluoro-3-methyl-alkanoyloxy, 2- or 3-chloro-alkoxy, 2- or 3-chloro-alkanoyloxy, 2-chloro-3-methyl-alkanoyloxy, 1- or 2-cyanoalkyl, 1- or 2-cyanoalkoxy, 2- or 3-cyano-alkanoyloxy, 1-, 2- or 3-methylalkyl, 1-, 2- or 3-methylalkoxy, 2- or 3-methylalkanoyloxy, 1-, 2- or 3-trifluoromethyl-alkanoyloxy, 1,2-epoxyalkyl, 2,3-epoxyalkoxy, 2,3-epoxy-alkanoyloxy, 1-alkoxycarbonylethyl, 1-alkoxycarbonyl-ethoxy, 2-alkoxy-propanoyloxy, (1-methylalkoxy)-carbonyl, (1-trifluoromethyl-alkoxy)-carbonyl, 1-alkoxy-2,2,2-trifluoroethyl, or ω-trifluoromethyl-ω-alkoxyalkyl with in each case 5 to 12 carbon atoms.

11. A compound according to claim 7, wherein $Y^2$ is a single bond, —O— or —OOC—; and R is a straight-chain or branched (racemic) alkyl or alkenyl residue with 5 to 12 carbon atoms in which a methylene group not adjacent to $Y^2$ can be replaced by —O—, —COO— or —OOC—, in which at least one hydrogen atom can be replaced by fluorine, and in which a terminal hydrogen atom can be replaced by cyclopentyl.

12. A compound according to claim 10, wherein R is a straight-chain or methyl-branched alkyl or alkenyl residue with 5 to 12 carbon atoms.

13. A compound according to claim 1, wherein n is 0.

14. A compound according to claim 13, wherein A is 1,4-phenylene and B is pyridine-2,5-diyl.

15. A compound according to claim 14, wherein the compound is 5-heptyl-2-[4-(8-cyclopentyl-octyloxy)-phenyl]-pyridine.

16. A compound according to claim 14, wherein the compound is 5-nonyl-2-[4-(8-cyclopentyl-octyloxy]-phenyl]-pyridine.

17. A compound according to claim 14, wherein the compound is 5-heptyl-2-[4-(7-cyclopentyl-heptyloxy)-phenyl]-pyridine.

18. A compound according to claim 14, wherein the compound is 5-nonyl-2-[4-(7-cyclopentyl-heptyloxy)-phenyl]-pyridine.

19. A compound according to claim 13, wherein A is 1,4-phenylene and B is pyrimidine-2,5-diyl.

20. A compound according to claim 19, wherein the compound is 5-octyl-2-[4-(8-cyclopentyl-octyloxy)-phenyl]-pyrimidine.

21. A compound according to claim 19, wherein the compound is 5-nonyl-2-[4-(8-cyclopentyl-octyloxy)-phenyl]-pyrimidine.

22. A compound according to claim 19, wherein the compound is 5-octyl-2-[4-(7-cyclopentyl-heptyloxy)-phenyl]-pyrimidine.

23. A compound according to claim 19, wherein the compound is 5-nonyl-2-[4-(7-cyclopentyl-heptyloxy)-phenyl]-pyrimidine.

24. A compound according to claim 19, wherein the compound is 5-nonyloxy-(2-[4-(8-cyclopentyl-octyloxy)-phenyl]-pyrimidine.

25. A compound according to claim 19, wherein the compound is 5-decyloxy-2-[4-(8-cyclopentyl-octyloxy)-phenyl]-pyrimidine.

26. A compound according to claim 19, wherein the compound is 5-octyloxy-2-[4-(7-cyclopentyl-heptyloxy)-phenyl]-pyrimidine.

27. A compound according to claim 19, wherein the compound is 5-nonyloxy-2-[4-(7-cyclopentyl-heptyloxy)-phenyl]-pyrimidine.

28. A compound according to claim 19, wherein the compound is 5-decyloxy-2-[4-(7-cyclopentyl-heptyloxy)-phenyl]-pyrimidine.

29. A compound according to claim 19, wherein the compound is 5-(8-cyclopentyl-octyloxy)-2-[4-(8-cyclopentyl-octyloxy)-phenyl]-pyrimidine.

30. A compound according to claim 13, wherein A is pyrimidine-2,5-diyl.

31. A compound according to claim 30, wherein the compound is 5-(7-cyclopentyl-heptyloxy)-2-(4-octyloxy-phenyl)-pyrimidine.

32. A compound according to claim 1, wherein n is 1.

33. A compound according to claim 32, wherein the compound is 5-(8-cyclopentyl-octyloxy)-2-[4'-hexyl-biphenyl-1-4-yl]-pyrimidine.

34. A liquid crystalline mixture comprising at least one compound of the formula

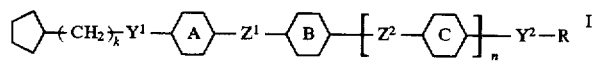

wherein k is a whole number of 4 to 18;

n is 0 or 1;

$Y^1, Y^2$ is a single bond, —O—, —COO— or —OOC—;

rings A, B, C each independently are 1,4-phenylene, pyrimidine-2,5-diyl, pyridine-2,5-diyl, pyrazine-2,5-diyl, naphthalene-2,6-diyl, quinoline-2,6-diyl, thiophene-2,5-diyl, thiazole-2,5-diyl or 1,3,4-thiadiazole-2,5-diyl, which are unsubstituted, mono or difluorinated, and ring C also is trans-1,4-cyclohexylene or trans-1,3-dioxane-2,5-diyl;

$Z^1$ is a single bond, —COO—, —OOC— or —C≡C—;

$Z^2$ is —COO—, —OOC—, —OCH$_2$—, —CH$_2$O— or —(CH$_2$)$_2$—; and

R is straight-chain or branched, optically inactive or optically active, alkyl or alkenyl with 4 to 20 carbon atoms in which one or two non-adjacent methylene groups can be replaced independently by —O—, —COO—, —OOC— or epoxyethylene, in which one or more hydrogen atoms can be replaced by fluorine, in which one hydrogen atom can be replaced by chlorine or cyano, and in which a terminal hydrogen atom can be replaced by cyclopentyl).

35. A liquid crystalline mixture in accordance with claim 34, wherein rings A, B and C each independently are 1,4-phenylene, 2- or 3-fluoro-1,4-phenylene, 2,3-difluoro-1,4-phenylene, pyrimidine-2,5-diyl, pyridine-2,5-diyl or pyrazine-2,5-diyl and ring C also signifies trans-1,4-cyclohexylene or trans-1,3-dioxane-2,5-diyl.

36. A liquid crystalline mixture in accordance with claim 34, wherein at least one of rings A, B and C is 1,4-phenylene, 2- or 3-fluoro-1,4-phenylene or 2,3-difluoro-1,4-phenylene and a maximum of one of rings A, B and C is pyrimidine-2,5-diyl, pyridine-2,5-diyl or pyrazine-2,5-diyl.

37. A liquid crystalline mixture in accordance with claim 34, wherein the compound of formula I is a compound of the formula

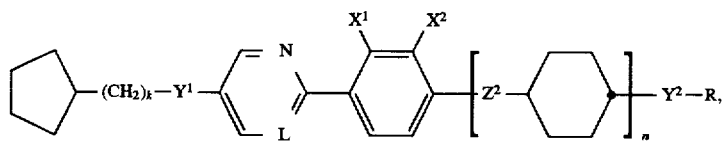

-continued

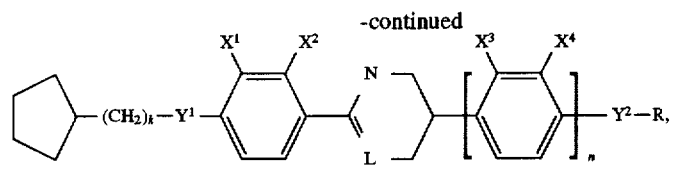
Ib

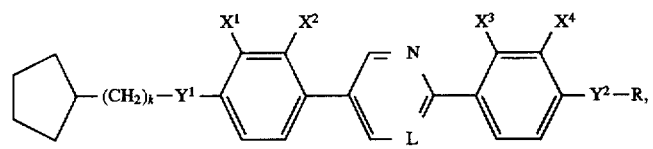
Ic

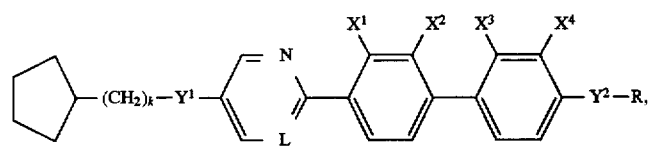
Id

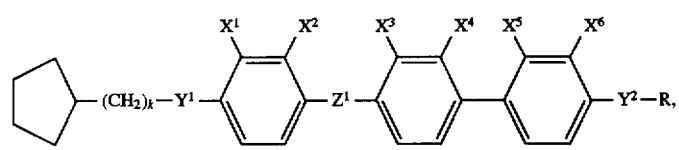
Ie

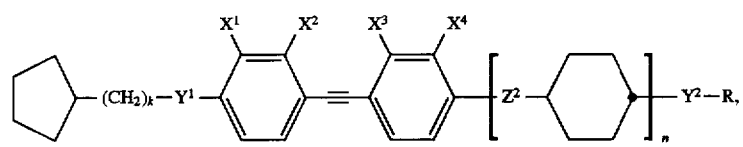
If

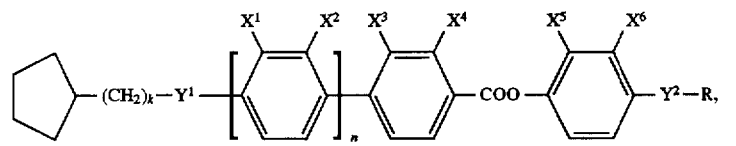
Ig

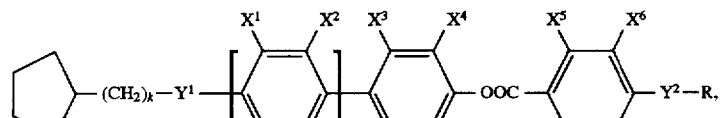
Ih

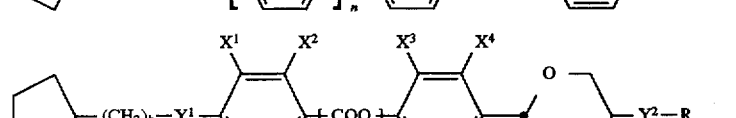
Ii

wherein

L is nitrogen or —CH=;
$X^1$-$X^6$ are, independently, hydrogen or fluorine; and p is 0 or 1.

38. A liquid crystalline mixture in accordance with claim 37, wherein k is a whole number of 5 to 12.

39. A liquid crystalline mixture in accordance with claim 38, wherein $Y^1$ is a single bond, —O— or —COO—.

40. A liquid crystalline mixture in accordance with claim 39, wherein $Y^1$ is —O—.

41. A liquid crystalline mixture in accordance with claim 40, wherein R is an alkyl or alkenyl residue with 5 to 12 carbon atoms in which 1 or 2 non-terminal methylene groups are replaced independently by —C*H(W)—, —C*F(CH$_3$)— or epoxyethylene, and in which 1 or 2 non-adjacent methylene groups can be replaced independently by —O—, —COO—, —OOC—; wherein W is fluorine, chlorine, cyano, methyl or trifluoromethyl and C* is a chiral centre.

42. A liquid crystalline mixture in accordance with claim 41, wherein —$Y^2$—R is an optically active group.

43. A liquid crystalline mixture in accordance with claim 42, wherein —$Y^2$—R is 2- or 3-fluoroalkyl, 2- or 3-fluoroalkoxy, 2,3-difluoroalkoxy, 2- or 3-fluoro-alkanoyloxy, 2,3-difluoroalkanoyloxy, 2-fluoro-2-methyl-alkanoyloxy, 2-fluoro-3-methylalkanoyloxy, 2- or 3-chloro-alkoxy, 2- or 3-chloro-alkanoyloxy, 2-chloro-3-methyl-alkanoyloxy, 1- or 2-cyanoalkyl, 1- or 2-cyanoalkoxy, 2- or 3-cyano-alkanoyloxy, 1-, 2- or 3-methylalkyl, 1-, 2- or 3-methylalkoxy, 2- or 3-methyl-alkanoyloxy, 1-, 2- or 3-trifluoromethyl-alkanoyloxy, 1,2-epoxy-alkyl, 2,3-epoxyalkoxy, 2,3-epoxy-alkanoyloxy, 1-alkoxycarbonyl-ethyl, 1-alkoxycarbonylethoxy, 2-alkoxy-propanoyloxy, (1-methyl-alkoxy)-carbonyl, (1-trifluoromethyl-alkoxy)-carbonyl, 1-alkoxy-2,2,2-trifluoroethyl, or ω-trifluoromethyl-ω-alkoxyalkyl with in each case 5 to 12 carbon atoms.

44. A liquid crystalline mixture in accordance with claim 40, wherein $Y^2$ is a single bond, —O— or —OOC—; and R is a straight-chain or branched (racemic) alkyl or alkenyl residue with 5 to 12 carbon atoms in which a methylene group not adjacent to $Y^2$ can be replaced by —O—, —COO— or —OOC—, in which at least one or more hydrogen atoms can be replaced by fluorine, and in which a terminal hydrogen atom can be replaced by cyclopentyl.

45. A liquid crystalline mixture in accordance with claim 34, which contains as additional components one or more compounds of the formulas

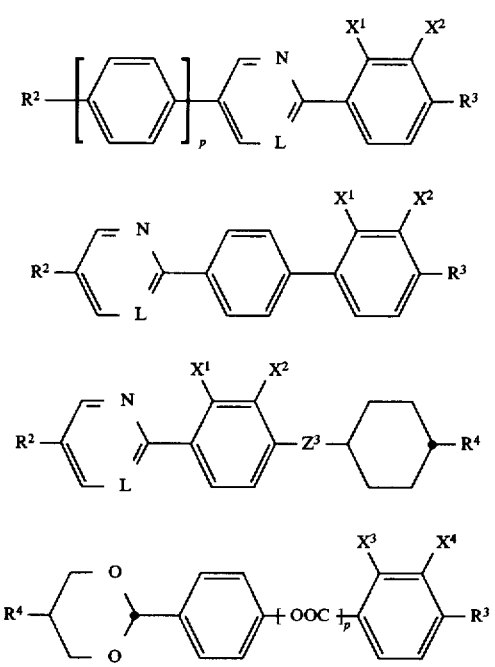

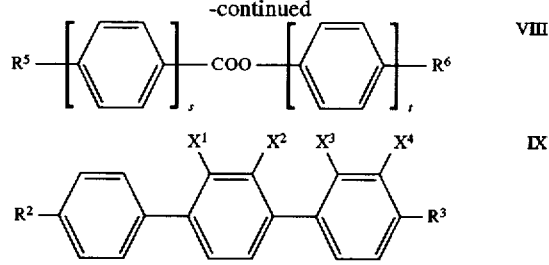

wherein p signifies 0 or 1;

s,t are 1 or 2, provided that s+t=2 or 3;

L signifies nitrogen or —CH=;

$X^1$, $X^2$, $X^3$, $X^4$ each independently signify hydrogen or fluorine;

$Z^3$ signifies a single bond, —OOC—, —OCH$^2$— or —(CH$_2$)$_2$—;

$R^2$, $R^3$ each independently signify alkyl, alkenyl, alkoxy, alkoxyalkyl, alkenoyloxy, alkanoyloxy, alkenoyloxy, alkoxyalkoxy, alkoxycarbonyl or alkenyloxycarbonyl;

$R^4$ signifies alkyl or alkenyl; and $R^5$, $R^6$ each independently signify alkyl, alkenyl, alkoxy or alkenyloxy.

46. A liquid crystalline mixture in accordance with claim 45, which contains one or more optically active compounds from the group of compounds of the general formulae

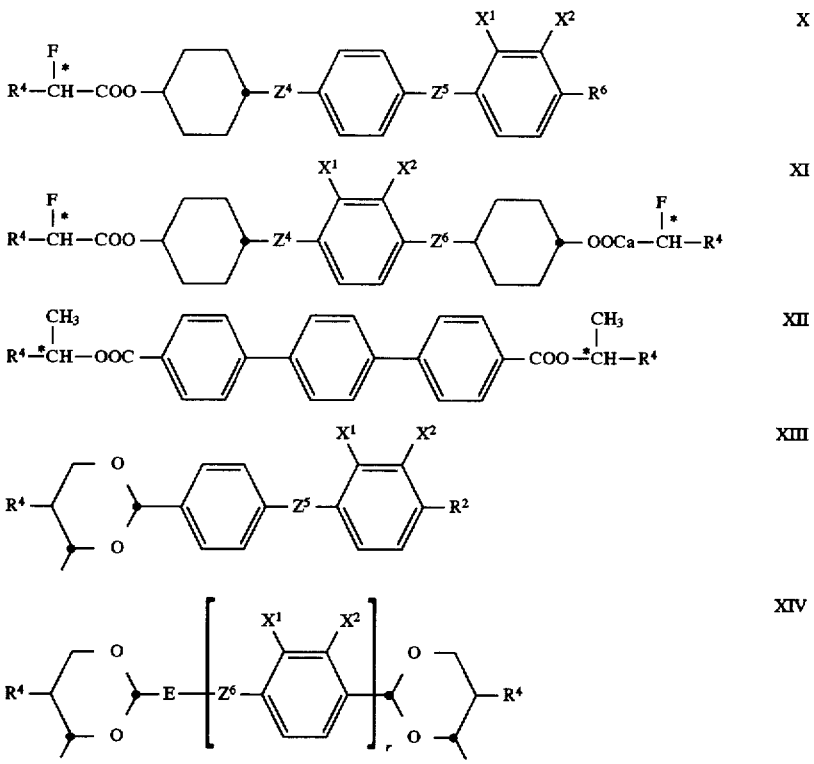

wherein

E signifies 1,4-phenylene or trans-1,4-cyclohexylene;

r signifies 0, 1 or 2;

$Z^4$ signifies a single bond, —(CH$_2$)$_2$— or —CH$_2$O—;

$Z^5$ signifies a single bond, —OCH$_2$—, —COO— or —OOC—; and $Z^6$ signifies a single bond, —(CH$_2$)$_2$— or —OCH$_2$—.

* * * * *